US00PP37307P2

(12) United States Plant Patent
Danziger

(10) Patent No.: US PP37,307 P2
(45) Date of Patent: Mar. 3, 2026

(54) ***PETUNIA* PLANT NAMED 'DPETCPFCLC'**

(50) Latin Name: ***Petunia* spp.**
Varietal Denomination: DPETCPFCLC

(71) Applicant: Danziger "DAN" Flower Farm, Beit Dagan (IL)

(72) Inventor: Gavriel Danziger, Israel (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 18/967,936

(22) Filed: Dec. 4, 2024

(51) Int. Cl.
*A01H 5/02* (2018.01)

(52) U.S. Cl.
USPC ..... Plt./356.21

(58) Field of Classification Search
USPC ..... Plt./356.13, 356.21
CPC . A01H 5/02; A01H 5/00; A01H 6/824; A01H 6/82
See application file for complete search history.

(56) References Cited

PUBLICATIONS

Ball Seed Blog Cast 2024 Wrap-Up, retrieved on Jul. 16, 2025 at https://www.ballseed.com/blog/2024/05/16/cast-2024-wrap-up.html, 4 pp. (Year: 2024).*
BFG Supply Know Nursery Inc. 2024-2025 Program, retrieved on Jul. 16, 2025 at https://www.bfgsupply.com/media/10423/2025-knox-nursery-product-program.pdf, 5 pp. (Year: 2025).*
Danziger Capella Fuchsia Lace, retrieved on Jul. 16, 2025 at https://www.danzigeronline.com/catalog/annuals/capella-fuchsia-lace/, one page. (Year: 2025).*
Garden Center, 2024 California Spring Trials Preview: Danziger, retrieved on Jul. 16, 2025 at https://www.gardencentermag.com/page/danziger-california-spring-trials/, 11 pp. (Year: 2024).*
Lawn & Garden Retailer, Danzifer offers preview of 2024 Cast display, retrieved on Jul. 16, 2025 at https://lgrmag.com/news/danziger-offers-preview-of-2024-cast-display/, 5 pp. (Year: 2024).*

* cited by examiner

*Primary Examiner* — June Hwu

(57) ABSTRACT

A new and distinct cultivar of *Petunia* plant named 'DPETCPFCLC' is disclosed, characterized by abundant, dark purple-pink flowers. Plants have a mounded habit, and bright green foliage. The new variety is a *Petunia*, normally produced as an outdoor garden or container plant.

2 Drawing Sheets

Figure 1:
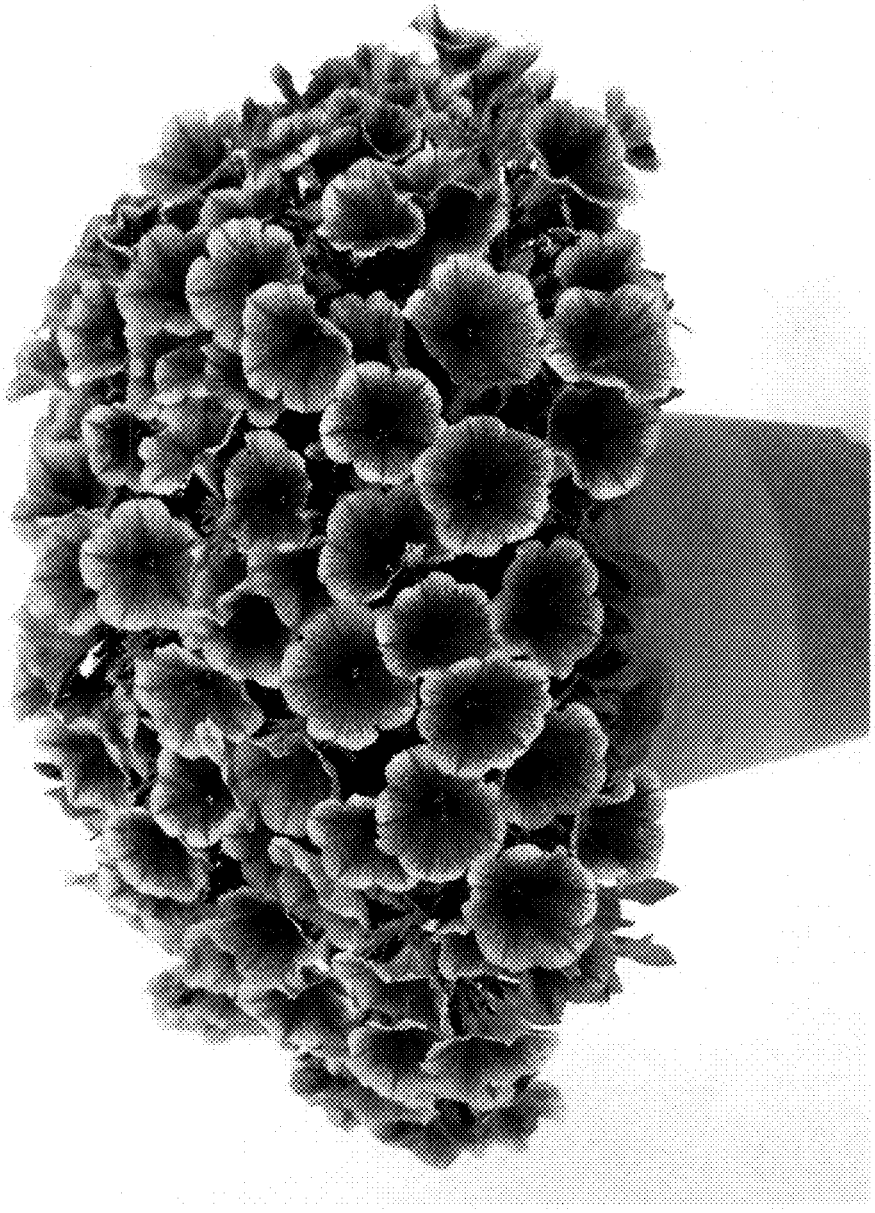

Latin name of the genus and species: *Petunia* spp.
Variety denomination: 'DPETCPFCLC'.

BACKGROUND OF THE INVENTION

The new *Petunia* cultivar is a product of a planned breeding program conducted by the inventor, Gavriel Danziger in Moshav Mishmar Hashiva, Israel. The objective of the breeding program was to produce new *Petunia* varieties for ornamental purposes. The seed parent is an unpatented internal *Petunia* selection referred to as 'PE-17-6190'. The pollen parent is an unpatented internal *Petunia* selection referred to as 'PE-17-6211'. The crossing resulting in this new variety was made in April 2021.

The new variety was found and selected in November 2021 by the inventor in a group of seedlings resulting from the crossing at the same nursery in Moshav Mishmar Hashiva, Israel.

Asexual reproduction of the new cultivar 'DPETCPFCLC' was first performed by terminal vegetative cuttings in November 2021, in Moshav Mishmar Hashiva, Israel. Subsequent propagation by vegetative cuttings has shown that the unique features of this cultivar are stable and reproduced true to type in more than 6 successive generations.

SUMMARY OF THE INVENTION

The cultivar 'DPETCPFCLC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPETCPFCLC' These characteristics in combination distinguish 'DPETCPFCLC' as a new and distinct *Petunia* cultivar:

1. Unique dark pink-purple flower color.
2. Mounded habit.
3. Abundant flowering.

PARENT COMPARISONS

Plants of the new cultivar 'DPETCPFCLC' are similar to the seed parent in most horticultural characteristics; however, 'DPETCPFCLC' differs in the following:

1. Growth habit of the new variety is mounded, while the growth habit of the seed parent is semi-trailing.
2. Plants of the new variety produce more flowers than plants of the seed parent.

Plants of the new cultivar 'DPETCPFCLC' are similar to the pollen parent in most horticultural characteristics; however, 'DPETCPFCLC' differs in the following:

1. Growth habit of the new variety is mounded, while the growth habit of the pollen parent is more upright.

COMMERCIAL COMPARISONS

Plants of the new cultivar 'DPETCPFCLC' can be compared to the commercial variety *Petunia* 'Cascadias Purple Ice', unpatented. These varieties are similar in most horticultural characteristics; however, 'DPETCPFCLC' differs in the following:

1. Flower color of the new variety is dark purple-pink, while the flower color of this comparator is purple.
2. Growth habit of the new variety is mounded, while the growth habit of this comparator is more spreading.

Plants of the new cultivar 'DPETCPFCLC' can also be compared to the commercial variety *Petunia* 'DPECAPNKLC', U.S. Plant Pat. No. 30,929. These varieties are similar in most horticultural characteristics; however, 'DPETCPFCLC' differs in the following:

1. Flowers of the new variety are larger than flowers of this comparator.
2. Flower color of the new variety is dark purple-pink, while the flower color of this comparator is light pink.
3. Growth habit of the new variety is mounded, while the growth habit of this comparator is more spreading.

BRIEF DESCRIPTION OF THE PHOTOGRAPHS

The accompanying photograph in FIG. 1 illustrates in full color a typical plant of 'DPETCPFCLC' grown in a 16 cm pot in Moshav Mishmar Hashiva, Israel.

Figure 2:
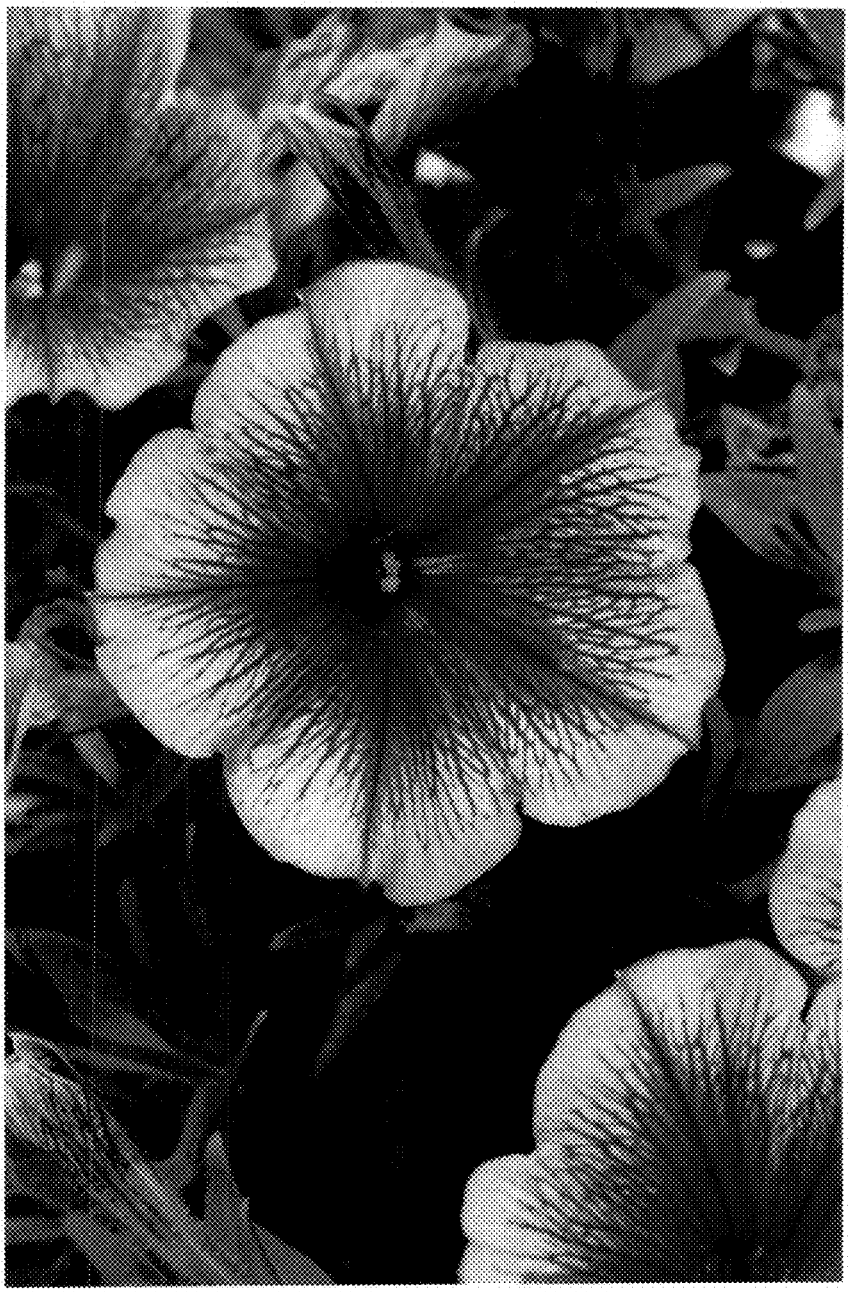

FIG. 2 illustrates in full color a close-up view of a typical flower of 'DPETCPFCLC' Age of the plant photographed is approximately 3 months from a rooted cutting in a 16 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPETCPFCLC' plants grown in a greenhouse in Moshav Mishmar Hashiva, Israel, under natural lighting. Measurements were taken during spring, summer, and autumn. The plants were approximately 12 weeks old from a rooted cutting in a 12 cm pot. The growing temperature ranged from approximately 20° C. to 35° C. during the day, 17° C. to 23° C. during the night. Measurements and numerical values represent averages of typical plant types. Botanical classification: *Petunia* spp. 'DPETCPFCLC'.

PROPAGATION

Total rooting time: 10 to 14 days at approximately 20° C.
Root description: Fibrous.

PLANT

Growth habit: Mounded.
Pot size of plant described: 12 cm.
Height: About 12 cm to top of flowers.
Plant spread: About 29 cm.
Growth rate: Medium.
Branching characteristics:
Length of primary lateral branches: 20 cm.
Diameter of lateral branches: About 0.3 cm.
Quantity of primary lateral branches: 8.
Characteristics of primary lateral branches:
*Form*.—Cylindrical.
*Diameter*.—About 0.3 cm.
*Color*.—RHS Yellow-Green 144B.
*Texture*.—Pubescent.
*Strength*.—Good.
Internode length: About 1.5 cm.

FOLIAGE

Leaf:
*Arrangement*.—Opposite.
*Quantity*.—Approximately 30 per branch.
*Average length*.—5.5 cm.
*Average width*.—3 cm.
*Shape of blade*.—Elliptic.
*Apex*.—Acute.
*Base*.—Acute.
*Margin*.—Entire.
*Texture of top surface*.—Velvety.
*Texture of bottom surface*.—Pubescent.
*Color*.—Young foliage upper side: RHS Yellow-Green 146A. Young foliage under side: RHS Yellow-Green 146B. Mature foliage upper side: RHS Yellow-Green 146A. Mature foliage under side: RHS Yellow-Green 146B.
*Venation*.—Type: Pinnate. Venation color upper side: RHS Yellow-Green 146C. Venation color under side: RHS Yellow-Green 146D.
*Petiole*.—Length: 0.8 cm. Diameter: 0.4 cm. Color: RHS Yellow-Green 146B. Texture: Velvety.

FLOWER

Bloom period: Spring, summer, and autumn.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3 to 6 days.
Approximate quantity of flowers per plant: About 80.
Lobing: Weak.
Persistence: Self-cleaning.
Bud:
*Shape*.—Tubular.
*Length*.—3.8 cm.
*Diameter*.—0.7 cm.
*Color*.—RHS Yellow-Green N144A.
Flower size:
*Diameter*.—6 cm.
*Flower tube length*.—2.5 cm.
*Flower tube diameter at distal end*.—1.2 cm.
*Flower tube diameter at proximal end*.—0.3 cm.
Petals:
*Length from throat*.—About 2 cm.
*Width*.—2.5 cm.
*Quantity*.—5.
*Texture*.—Velvety.
*Apex*.—Blunt.
*Margin*.—Entire.
*Vein conspicuousness*.—Strong from base of petal until about 20% from margin, then weak.
*Color*.—When opening: Upper surface: RHS Red-Purple 59C fading out into a background color of 73D with conspicuous veins 59C until 10% to 20% distance from margin, then almost entirely 73D. Lower surface: RHS Red-Purple N57D with conspicuous veins 59D. Fully opened: Upper surface: RHS Red-Purple 59D fading out into a background color of 65D with conspicuous veins 59C until 10 to 20% distance from margin, then almost entirely 65D. Lower surface: RHS Red-Purple 59D with conspicuous veins 59D. Flower throat (inside): RHS Purple 75C covered with veins 59B. Flower throat, vein: RHS Red-Purple 59B. Flower tube (outside): RHS Yellow-Green 151D. Flower tube, vein: RHS Yellow-Green 144A. Fading: RHS Red-Purple 61D fading out into a background color of 65D with conspicuous veins 61D until 10 to 20% distance from margin, then almost entirely 65D.

Calyx/sepals:

*Quantity per flower.*—5.

*Shape.*—Linear.

*Length.*—About 1.5 cm.

*Width.*—About 0.2 cm.

*Apex.*—Acute.

*Base.*—Cuneate.

*Margin.*—Entire.

*Texture.*—Velvety all surfaces.

*Color.*—Upper Surface: RHS Yellow-Green 146A. Lower Surface: RHS Yellow-Green 146B.

Peduncle:

*Length.*—About 2.5 cm.

*Diameter.*—About 0.2 cm.

*Color.*—RHS Yellow-Green 146C.

*Orientation.*—45°.

Fragrance: None.

REPRODUCTIVE ORGANS

Stamens:

*Number.*—5.

*Filament length.*—2 cm.

Anthers:

*Length.*—0.2 cm.

*Shape.*—Rounded.

*Color.*—RHS Yellow 1C.

*Pollen.*—Color: RHS Yellow 4D. Quantity: Abundant.

Pistil:

*Number.*—1.

*Length.*—About 2.2 cm.

*Style.*—Length: About 1.8 cm. Color: RHS Yellow-Green 145B.

*Stigma.*—Shape: Rounded. Color: RHS Yellow-Green 145A. Ovary Color: RHS Yellow-Green 143C.

OTHER CHARACTERISTICS

Seeds and fruits: About 80 brown, rounded seeds of about 0.5 mm diameter, per one, brown, conical capsule.

Disease/pest resistance: Typical resistance and susceptibility to the normal diseases and pests of *Petunia*. Pests common to *Petunia* include Aphids and thrips. Typical diseases are *Botrytis* and *Pythium.*

Temperature tolerance: Tolerates a range between 5° C. to 40° C.

What is claimed is:

1. A new and distinct cultivar of *Petunia* plant named 'DPETCPFCLC' as herein illustrated and described.

* * * * *